US005770360A

United States Patent [19]
Kievits et al.

[11] Patent Number: 5,770,360
[45] Date of Patent: Jun. 23, 1998

[54] ELIMINATION OF FALSE NEGATIVES IN NUCLEIC ACID DETECTION

[75] Inventors: Tim Kievits, Vught; Peter Franklin Lens, Den Bosch, both of Netherlands

[73] Assignee: Akzo Nobel N.V., Arnhem, Netherlands

[21] Appl. No.: 392,932

[22] PCT Filed: Aug. 20, 1993

[86] PCT No.: PCT/EP93/02248

§ 371 Date: Feb. 24, 1995

§ 102(e) Date: Feb. 24, 1995

[87] PCT Pub. No.: WO94/04706

PCT Pub. Date: Mar. 3, 1994

[30] Foreign Application Priority Data

Aug. 24, 1992 [EP] European Pat. Off. .............. 92202563

[51] Int. Cl.[6] .............................. C12Q 1/68; C12Q 1/00; C12N 15/00
[52] U.S. Cl. .................................. 435/6; 435/4; 435/91.2; 935/77; 935/78
[58] Field of Search ....................................... 435/6, 91.2

[56] References Cited

U.S. PATENT DOCUMENTS

| | | | |
|---|---|---|---|
| 4,626,501 | 12/1986 | Landes | 435/6 |
| 4,965,188 | 10/1990 | Mullis et al. | 435/6 |
| 5,356,774 | 10/1994 | Axelrod et al. | 435/6 |
| 5,409,818 | 4/1995 | Davey et al. | 435/91.21 |
| 5,455,166 | 10/1995 | Walker | 435/91.2 |
| 5,457,027 | 10/1995 | Nadeau et al. | 435/6 |

FOREIGN PATENT DOCUMENTS

| | | |
|---|---|---|
| 0461496 A1 | 6/1991 | European Pat. Off. . |
| 0525882 A1 | 2/1993 | European Pat. Off. . |
| WO 89/07154 | 8/1989 | WIPO . |
| WO 91/02817 | 3/1991 | WIPO . |
| WO 92/01812 | 2/1992 | WIPO . |
| WO 93/10257 | 5/1993 | WIPO . |

OTHER PUBLICATIONS

Kwoh et al., PNAS 86: 1173–1177 (1989).
Walker et al., Nucleic Acids Research 20: 1691–1696 (1992).
Walker et al., PNAS 89: 392–396 (1992).
Guatelli et al., PNAS 87: 1874–1878 (1990).
Lizardi et al., Bio/Technology 6:1197–1202 (1988).
Wang et al. PNAS 86: 9717–9721 (1989).
Matthews et al. Analytical Biochemistry 169: 1–25 (1988).
Saiki et al. PNAS 86: 6230–6234 (1989).
Erlich et al., pp. 261–271 in "PCR Protocols" Ed. Innis et al., Academic Press (1991).
K.M. Tham et al., "Diagnostic Sensitivity of PCR and Southern Blot Hydridi–zation for the Detection of Human Papillomavirus DNA in Biopsy Specimens from Cervical Lesions," *Anatomic Pathology*, 95:5:638–646, May 1991.
J.P. Ursi et al., "Utility of an Internal Control for the polymerase chain reaction," *APMIS*, 100:635–639, 1992.
A.M. Wang et al., "Quantitation of mRNA by the polymerase chain reaction, " *Proc. Natl. Acad. Sci. USA*, 86:9727–9721, 1989.

*Primary Examiner*—Stephanie W. Zitomer
*Assistant Examiner*—Ethan Whisenant
*Attorney, Agent, or Firm*—Mary E. Gormley; William M. Blackstone

[57] ABSTRACT

The present invention relates to a method for the elimination of false negative test results in assays for the detection of amplified analyte nucleic acid in a sample. Prior to amplification, an internal control is added to the sample, comprising a nucleic acid distinguishable from the analyte nucleic acid, that can be amplified with the same amplification reagents as the analyte nucleic acid. Preferably the internal control comprises a nucleic acid sequence corresponding to the analyte nucleic acid that has been mutated to discriminate it from the analyte nucleic acid.

9 Claims, No Drawings

ELIMINATION OF FALSE NEGATIVES IN NUCLEIC ACID DETECTION

This application is a 371 of PCT/EP93/02248 filed 20 Aug. 1993, published as WO94/04706 Mar. 3, 1994.

FIELD OF THE INVENTION

The present invention relates to a method for the elimination of false negative test results in assays for the detection of amplified analyte nucleic acid.

Normally, when amplified nucleic acid is to be detected in a sample, negative test results, that is results indicating that no analyte nucleic acid was originally present in the sample under investigation, can only be confirmed by carrying out a separate confirmation assay. Since the performance of separate confirmation tests is a rather time consuming event the need exists for a method for providing a control on negative test results in assays for the detection of amplified analyte nucleic acid. When each sample can be provided with a direct internal check on the assaying procedures and the amplification method no separate confirmation tests have to be performed.

BACKGROUND OF THE INVENTION

The addition of other sequences to a sample comprising analyte nucleic acid, which are capable of being coamplified with the analyte nucleic acid, has been described by Becker and Hahlbrock (*Nucleic Acids Research*, Vol. 17. Number 22. 1989). The method described by Becker and Hahlbrock is a method for the quantification of nucleic acid where different known amounts of internal standard, comprising a nucleic acid sequence that differs from the analyte nucleic acid by just one nucleotide (point mutation) are added to a sample containing an unknown amount of analyte nucleic acid and coamplified by PCR with the analyte nucleic acid. By introducing one base change in the internal standard sequence a specific restriction site is created and the mutant sequence is cut with the appropriate restriction enzyme before the sample containing the amplified nucleic acid is applied to an electrophoretic gel. The nucleic acid is quantified by comparing the bands in the gel representing (a part of) the mutant sequence and the analyte nucleic acid.

Becker and Hahlbrook use the internal standard as a marker in their quantification method where both analyte and marker are non-competitively amplified.

SUMMARY OF THE INVENTION

The present invention relates to a method for the elimination of false negative test results in assays for the detection of amplified analyte nucleic acid in a sample characterized in that, prior to amplification, an internal control, comprising a nucleic acid distinguishable from the analyte nucleic acid, that can be amplified with the same amplification reagents as the analyte nucleic acid, is added to the sample. The reagents used with the amplification include the amplification primers. The internal control used with the method according to the invention should resemble the analyte nucleic acid in that both are capable of annealing with the same amplification primers.

When the sample is not provided with an internal control a negative test result will give no indication of the presence of amplified nucleic acid. In this case the absence of any signal representing amplified nucleic acid can also be caused by an error in the amplification or assaying procedures and a separate confirmation test must be performed to exclude this possibility.

One advantage of the use of a method with an internal control in every sample according to the invention is that in the case of a "negative" sample (that is a sample in which no analyte was present) a signal is obtained, indicating the presence of the amplified internal control. The appearance of the signal representing the internal control confirms the negative test result and serves as a control on the followed procedures (the amplification and the detection procedure). False negative test results are thereby excluded.

The internal control used with a method according to the invention must differ from the analyte in that, upon detection, the presence of the amplified internal control is indicated by a signal that differs from the signal representing the analyte. For example, with gel electrophoretic separation, the analyte and the internal control would be indicated by the appearance of bands at different running distances from the top of the gel. With a solid phase hybridization assay the presence of amplified analyte or internal control nucleic acid can be indicated by different spots on a solid phase.

DETAILED DESCRIPTION OF THE INVENTION

The method according to the invention can be used for the detection of any kind of nucleic acid optionally present in a sample for which suitable amplification primers can be constructed, RNA as well as DNA. For example, clinical (blood) samples can be tested on the presence of RNA from a virus like HIV, HCV or CMV.

The method according to the invention can be used with any kind of amplification technique, for example the so-called polymerase chain reaction (PCR) as described in U.S. Pat. Nos. 4,683,195 and 4,683,202. A preferred method for the amplification of nucleic acid is the "nucleic acid sequence based amplification (NASBA)" as disclosed in European Patent application EP 0,329,822.

The advantage of the use of NASBA over the use of, for example PCR, is that no denaturation step is required to obtain single stranded nucleic acid after amplification is completed, since NASBA generates (large amounts of) single stranded RNA from the nucleic acid originally present, where the nucleic acid originally present can be RNA as well as DNA. Another disadvantage of PCR, which generates double stranded DNA instead of single stranded RNA, is that after denaturation primers and second strands, complementary to the template, compete for the template during reannealing which lowers the sensitivity of the amplification.

With the method according to the invention the internal control is added, during sample preparation prior to amplification, in a defined amount. The amount of internal control added hardly disturbs the analyte nucleic acid amplification.

When an amplification method like NASBA is used it depends on the relative amount of the internal control added with respect to the amount of the analyte nucleic acid present in the sample which nucleic acid will be amplified preferably:

When the analyte nucleic acid is present in the sample in a larger or equal amount than the internal control (for example hundred molecules of the control are added to a sample containing more than thousand molecules of the analyte) the analyte nucleic acid will be amplified preferably. After amplification is completed the amount of the internal control will still be very low.

On the other hand, when the sample under investigation is negative for the analyte nucleic acid (meaning that the analyte nucleic acid, for example viral RNA, was not originally present in the sample) the internal control will be amplified and, since no competition for the amplification primers with a larger amount of analyte nucleic acid takes place, the control will be present in large detectable amounts after the amplification procedure is completed.

Preferably the internal control comprises a nucleic acid sequence corresponding to the analyte nucleic acid that has been mutated to discriminate it from the analyte nucleic acid.

The internal control may differ from the analyte in different ways depending on the detection procedures followed. In any case the nucleic acid used as internal control must resemble the analyte nucleic acid in that it should be capable of being amplified with the same amplification reagents as the analyte nucleic acid. The internal control can be mutated in different ways to discriminate it from the analyte nucleic acid. For example an insertion can be introduced, rendering an internal control that is longer than the analyte, or a deletion rendering a shorter internal control.

In any case it should be prevented that the internal control can, due to a mutation (e.g. a deletion), be amplified more efficiently than the analyte nucleic acid. Preferably an internal control is used that is amplified less efficiently than the analyte nucleic acid in order to prevent the internal control from interfering with the amplification of any analyte nucleic acid that might be present in a sample.

In one embodiment of the invention the internal control and the analyte resemble each other in that they are both capable of forming a detectable complex with one and the same complementary oligonucleotide. This oligonucleotide will hybridize to a part of the sequence of the analyte that is also present in the internal control.

In the case where the amplified nucleic acid (analyte or internal control) is detected with the aid of gel electrophoresis it is preferred to use an internal control that differs from the analyte nucleic acid in length. The length difference between the analyte and the internal control will result in different mobilities in an electrophoretic gel. Since the internal control differs in length from the analyte nucleic acid, the internal control will appear as a band with a running distance from the top of the gel that differs from the place a spot would appear characteristic for the analyte nucleic acid.

The running distance from the top of the gel therefore indicates whether the analyte or the internal control was amplified, where amplification of the internal control confirms the absence of detectable amounts of analyte nucleic acid in the sample.

When the amplified nucleic acid is subjected to electrophoresis the presence of nucleic acid in the gel can be indicated by any method known in the art. A well known method, known as "Southern blotting", comprises transferring the nucleic acid to nitrocellulose after electrophoresis and hybridizing it with a radio-labelled complementary probe. The nucleic acid can then be visualized by autoradiography.

Since the above described method is rather time consuming it is preferred to add a complementary oligonucleotide to the amplified nucleic acid prior to subjecting it to electrophoresis. Resulting complexes can now be separated from remaining free labelled probe by gel electrophoresis. When the detection probe is hybridized with the nucleic acid present in the sample prior to subjecting the sample to gel electrophoresis the detection probe will be added to the nucleic acid present after amplification (analyte or control). The detection probe, capable of hybridizing to the analyte as well as the internal control, will form a complex with the amplified nucleic acid present. Part of the amount of the oligonucleotides added will bind specifically to the amplified nucleic acid and the rest of the oligonucleotide added will remain as free labelled oligonucleotide and will be separated from the complexes during gel electrophoresis. This remaining free labelled probe will generally appear as a separate band at the bottom of the gel.

When the test result is negative (no analyte nucleic acid was present) still a band appears in the gel at a height characteristic for the size of the complex formed between the internal control and the labelled probe indicating that amplification and hybridization with the labelled probe actually took place. The negative (no nucleic acid to be detected present) result of the assay is thereby confirmed.

The detection probe can be labelled in different ways as long as a label is used that is capable of traversing the gel. The use of enzyme labelled probes, added to a sample containing nucleic acid to which it can be hybridized, to form detectable complexes that can be separated from the free enzyme labelled probe by gel electrophoresis has been described in co-owned co-pending U.S. patent application Ser. No. 07/910,860 the contents of which are incorporated herein by reference.

The enzyme labels as described in the above mentioned U.S. application, like for example horseradish peroxidase, retain its activity after being subjected to electrophoresis and locked in the gel system, and are still capable of reacting with an appropriate substrate to give a colour reaction by which the presence of the labelled nucleic acid (that is the enzyme labelled complex nucleic acid and/or the free enzyme labelled oligonucleotide) in the gel is indicated.

The system thus obtained is simple to use. No special instrumentation is required for the detection of the enzyme label in the gel and therefore very useful for diagnostic purposes, e.g. the testing of clinical samples on the presence of a certain nucleic acid originating from, for example, a certain virus.

After separation of the remaining free enzyme labelled oligonucleotide from the enzyme labelled complex nucleic acid by gel electrophoresis is completed, detection of the labelled complex in the gel is carried out by staining with an appropriate enzyme substrate.

The staining procedure is simple and fast. The gel is simply soaked in a solution comprising an appropriate enzyme substrate and a colour reaction takes place between the enzyme label present in the gel and the substrate solution. The substrate used will react with bands, containing enzyme-labelled nucleic acid, present in the gel. The colour reaction between the enzyme label and the substrate will take place on or in the gel and the presence of the colour on or in the gel, indicating the presence of enzyme activity, can be detected visually. Good results are obtained when the oligonucleotide is labelled with horseradish peroxidase or a derivative thereof, and detection takes place by staining labelled nucleic acid in the gel with 3,3',5,5'-tetramethylbenzidine//$H_2O_2$. Horseradish peroxidase (HRP) catalyses the conversion of hydrogenperoxide into water. Tetramethylbenzidine (TMB), a non-precipitating substrate for HRP, is a chromogenic substance that acts as electron donor for the conversion of hydrogen peroxide into water and is converted by the HRP into a coloured complex thereby indicating the presence of enzyme activity. The colour formed can be detected visually.

The staining procedure must be carried out under conditions where the enzyme is still active. The staining solution should have a pH value that is appropriate for the enzyme label used.

Electrophoretic buffers usually have a pH value that differs from the activity optimum of the enzyme. Therefore the gel has to be brought to the proper pH value for the enzyme reaction to take place by washing the gel with a buffer solution after it has been subjected to electrophoresis.

When HRP is used as enzyme label the gel can be directly stained after it has been subjected to electrophoresis in a buffer comprising the enzyme substrate (e.g. $TMB/H_2O_2$) and imidazol. Imidazol shifts the activity optimum for HRP to a higher pH value. Therefore, with the use of imidazol, the gel can be directly stained in the electrophoretic buffer and the time consuming washing procedure can be eliminated.

Since, with this embodiment of the method according to the invention, nucleic acid amplification may be coupled to an enzymatic signal amplification (each enzyme molecule will be able to convert many substrate molecules that will stay in/on the gel) a high sensitivity is obtained.

Of course the method according to the invention is not limited to the application as described above where the detection procedure comprises gel electrophoresis of the amplified nucleic acid. For example; the detection of amplified nucleic acid (analyte or internal control) can likewise be carried out using a complementary oligonucleotide, capable of reacting with both the analyte and the internal control, immobilized on a solid phase. In order to detect whether the analyte or the internal control is bound to the solid phase, two differently labelled detection probes now can be used. One will react specifically with the analyte bound to the solid phase (because it comprises an oligonucleotide that is complementary to part of the analyte nucleic acid) while the second labelled detection probe, comprising a label that can be distinguished from the label on the first detection probe, will react specifically with the internal control. The internal control used in this case must resemble the analyte in its capability of hybridizing to the immobilized oligonucleotide on the solid phase, but must differ from the analyte in that it will react with a different labelled detection probe than the analyte. This can be achieved by constructing an internal control by replacing the sequence complementary to a first labelled detection probe with a different nucleotide sequence that is not present in the analyte and is complementary to a second labelled detection probe. The kind of label bound to the solid phase will indicate whether the analyte or the internal control was present, thereby indicating whether the test result is positive or negative.

Another embodiment of the invention comprises immobilizing two different oligonucleotides, one binding specifically to the analyte and another specifically to the internal control, on a solid phase in two distinct spots. Any amplified nucleic acid that will bind to one of the spots on the solid phase can be detected by hybridizing it to a labelled oligonucleotide complementary to a sequence present in both the analyte nucleic acid and the internal control. In this case it is the spot on the solid phase on which the label will bind that indicates whether the test result is positive or negative. Depending on the detection method employed the label can be of any kind. For example, in the case the presence of amplified nucleic acid is detected with scattered total internal reflectance the label might be a gold sol particle, but also radio-labelled (detection by autoradiography) or enzyme labelled probes, that give a colour reaction with a suitable enzyme substrate, can be used.

The invention is further exemplified with the following examples:

EXAMPLE 1

Nucleic acid was extracted from specimens from AIDS patients. Full blood, plasma, monocytes and thrombocytes were used as starting material. Nucleic acid was extracted from whole blood samples of SCID-hu mice infected with HIV-1. The samples were processed according to the sample processing method as described by Boom et al. (*J. Clin. Microbiol.* 28: 495–503. 1990). RNA was amplified by using the extracted nucleic acid as input for NASBA. No templates were included as checks for the contamination and a series of different amounts of WT HIV-1 RNA ($10^1$, $10^2$, $10^3$, $10^4$ molecules) was used to determine detection sensitivity. A primer pair for the HIV-gene gag was used for amplification (Primer 1 (OT270): AATTCTAATACGACTCACTAT-AGGGGTGCTATGTCACTTCCCCCTTGGTTCTCTCA; Primer 2: (OT271) AGTGGGGGGACATCAAGCAGCCATGCAAA). In each amplification reaction 102 molecules of a RNA molecule is added for a control on the procedure. This RNA molecule (E2) comprises the same target sequence as the wild type HIV-1 RNA together with an 140 bp insertion that replaces a 22 bp Sph IxPst I fragment. Hybridization was performed for 10 minutes at 45° C. in a water bath. A 7% native acrylamide gel in a Biometra Multigel G44 configuration was used for separation of the hybridized and the non-hybridized HRP labelled oligonucleotide. 1*TBE (50 mM Tris, 50 mM Borate, 1 mM EDTA, pH 8,5) was used as running and gel buffer.

2,5 $\mu$l of the hybridized samples were put on the gel. The electrophoresis was stopped when xylene cyanol reached 70% of the gel length. After gel electrophoresis was completed the gel was washed and rocked in citrate buffer pH 5,0 for 5 minutes. Subsequently the gel was washed and rocked in citrate buffer pH 5,0 containing 1% dextran sulphate for 15 minutes prior to being rocked and washed for two minutes in citrate buffer pH 5,0 again. HRP containing bands were visualised by staining with TMB (0.1 mg/ml) and $H_2O_2$ (1 $\mu$l 30% $H_2O_2$ per 10 ml) for 10 minutes. The gel was rinsed with water and incubated (dehydrated) for at least two hours in 50% methanol. Afterwards the gel was dried for two hours at 50° C. under vacuum in a gel dryer (Bio-rad model 583). In table 1 the visually scored results are summarized.

TABLE 1

AIDS patients no. 48, 49 and 50.

| patient | specimen | 1st WT | 1st E2 | 2nd WT | 2nd E2 | comment |
|---|---|---|---|---|---|---|
| 48 | full blood | + | − | + | − | positive |
|  | plasma | + | − | + | − | positive |
|  | monocytes | + | − | + | − | positive |
|  | thrombocytes | + | − | + | − | positive |
| 49 | full blood | + | − | + | − | positive |
|  | plasma | + | − | + | − | positive |
|  | monocytes | − | − | + | − | indeterminate |
|  | thrombocytes | − | − | + | − | indeterminate |
| 50 | full blood | + | − | + | − | positive |
|  | plasma | + | − | + | − | positive |
|  | monocytes | + | − | + | − | positive |
|  | thrombocytes | − | + | − | + | negative |
| control | $10^2$ | − | + |  |  | negative |
|  | $10^3$ | + | − |  |  | positive |
|  | $10^4$ | + | − |  |  | positive |
|  | $10^5$ | + | − |  |  | positive |
|  | $10^6$ | + | − |  |  | positive |
|  | NT-1 | − | + |  |  | negative |
|  | NT-2 | − | + |  |  | negative |
|  | NT-3 | − | + |  |  | negative |

EXAMPLE 2

The indeterminate scores from the first example were retested in another experiment which was performed in the same way as the experiments described in Example 1. The indeterminate samples from the first example all scored positive when retested. Also the control with the lowest amount of input molecules ($10^2$) now scored positive. From these results it can be concluded that these experiment yielded a somewhat higher sensitivity than the experiments of the first example. The results are given in Table 2.

TABLE 2 retesting of undetermined results of table 1.

| patient | specimen | 1st WT | 1st E2 | 2nd WT | 2nd E2 | comment |
|---|---|---|---|---|---|---|
| 49 | monocytes | + | − | + | − | positive |
|  | thrombocytes | + | − | + | − | positive |
| control | $10^2$ | + | − |  |  | positive |
|  | $10^3$ | + | − |  |  | positive |
|  | $10^4$ | + | − |  |  | positive |
|  | $10^5$ | + | − |  |  | positive |
|  | $10^6$ | + | − |  |  | positive |
|  | NT-1 | − | + |  |  | negative |
|  | NT-2 | − | + |  |  | negative |

We claim:

1. A method for the elimination of false negative results in an isothermal transcription-based amplification reaction, comprising:
   (a) performing an isothermal transcription-based amplification of an analyte nucleic acid in a sample to which an internal control nucleic acid has been added, wherein the internal control nucleic acid is amplified less efficiently than the analyte nucleic acid such that the analyte nucleic acid will be preferentially amplified when present in said sample in an amount larger or equal to the amount of internal control nucleic acid, and wherein both the internal control and analyte nucleic acids are amplified with the same amplification reagents; and
   (b) detecting the RNA amplification products and determining whether only the internal whether only the internal control nucleic acid has been amplified,
   whereby detection of only the internal control nucleic acid amplification products confirms a negative test result for the analyte nucleic acid.

2. A method according to claim 1, wherein the internal control comprises a nucleic acid sequence corresponding to the analyte nucleic acid that has been mutated to discriminate it from the analyte nucleic acid.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "DNA primer"

( i i i ) HYPOTHETICAL: NO ( i v ) ANTI-SENSE: YES ( x i ) SEQUENCE DESCRIPTION: SEQ ID NO:1:

AATTCTAATA CGACTCACTA TAGGGGTGCT ATGTCACTTC CCCCTTGGTT CTCTCA     56

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "DNA primer"

( i i i ) HYPOTHETICAL: NO ( i v ) ANTI-SENSE: YES ( x i ) SEQUENCE DESCRIPTION: SEQ ID NO:2:

AGTGGGGGGA CATCAAGCAG CCATGCAAA     29

3. A method according to claim 1, wherein the internal control is longer than the analyte nucleic acid.

4. A method according to claim 1, wherein the internal control and the analyte nucleic acid will both form a detectable complex with the same complementary oligonucleotide.

5. A method according to claim 4, wherein the complementary oligonucleotide is immobilized on a solid phase and each of the detectable complexes will react with differently labeled reactants.

6. A method according to claim 1, wherein the analyte nucleic acid and the internal control nucleic acid will each form a detectable complex with a different complementary oligonucleotide.

7. A method according to claim 6, wherein said different complementary oligonucleotides are each immobilized at a different spot on a solid phase.

8. The method according to claim 3, wherein the RNA products from step (b) are detected by reacting them with an enzyme-labeled probe that will bind to amplified nucleic acid generated from the analyte nucleic acid or the internal control nucleic acid to form complexes, followed by subjecting the complexes to gel electrophoresis to separate them from any remaining free enzyme-labeled probes, and reacting the gel with an appropriate substrate, whereby the presence of complexes comprising the amplified product from the analyte nucleic acid or complexes comprising amplified product derived from the internal control is determined according to their positions on the gel.

9. The method according to claim 8, wherein the enzyme label is horseradish peroxidase and the substrate is 3,3',5,5'-tetramethylbenzidine.

* * * * *

UNITED STATES PATENT AND TRADEMARK OFFICE
CERTIFICATE OF CORRECTION

PATENT NO. : 5,770,360
DATED : June 23, 1998
INVENTOR(S) : Kievits et al.

It is certified that error appears in the above-identified patent and that said Letters Patent is hereby corrected as shown below:

Claim 1, line 16, delete the first instance of "whether only the internal".

Signed and Sealed this

First Day of September, 1998

Attest:

BRUCE LEHMAN

*Attesting Officer*    *Commissioner of Patents and Trademarks*